(12) United States Patent
Tani (10) Patent No.: US 7,891,899 B2
(45) Date of Patent: *Feb. 22, 2011

(54) APPLICATOR

(75) Inventor: Yoshikazu Tani, Tokyo (JP)

(73) Assignee: Tokiwa Corporation, Nakatsugawa-Shi, Gifu (JP)

( * ) Notice: Subject to any disclaimer, the term of this patent is extended or adjusted under 35 U.S.C. 154(b) by 823 days.

This patent is subject to a terminal disclaimer.

(21) Appl. No.: 11/494,604

(22) Filed: Jul. 28, 2006

(65) Prior Publication Data

US 2007/0020038 A1 Jan. 25, 2007

Related U.S. Application Data

(63) Continuation of application No. 10/914,144, filed on Aug. 10, 2004, now Pat. No. 7,168,878.

(30) Foreign Application Priority Data

Sep. 18, 2003 (JP) .............................. 2003-326695

(51) Int. Cl.
*B05C 11/00* (2006.01)
(52) U.S. Cl. .................. 401/266; 401/265; 401/263; 401/270
(58) Field of Classification Search ................ 401/265, 401/268–288, 261–263, 266
See application file for complete search history.

(56) References Cited

U.S. PATENT DOCUMENTS

| | | | |
|---|---|---|---|
| 1,137,086 A * | 4/1915 | Rodiger | ...................... 401/262 |
| 3,094,130 A | 6/1963 | Wiener | |
| 4,279,527 A * | 7/1981 | Moe et al. | .................... 401/186 |
| 4,726,386 A | 2/1988 | Schultz | |
| 4,748,990 A | 6/1988 | Brown et al. | |
| 4,902,152 A | 2/1990 | Seidler | |
| 5,222,824 A | 6/1993 | Nicoll et al. | |
| 5,345,644 A | 9/1994 | Gueret | |
| 5,397,195 A * | 3/1995 | Goncalves | ................... 401/277 |
| 5,772,347 A * | 6/1998 | Gueret | ........................ 401/266 |
| 5,857,796 A * | 1/1999 | Waldmann | ................... 401/277 |
| 6,315,478 B1 | 11/2001 | Atkins | |
| 6,641,320 B1 * | 11/2003 | Ballot et al. | ................. 401/270 |

* cited by examiner

*Primary Examiner*—David J. Walczak
*Assistant Examiner*—Keegan Gumbs
(74) *Attorney, Agent, or Firm*—Bacon & Thomas, PLLC (57) ABSTRACT

To prevent leakage, excessive discharge and stagnation of a liquid material applied by an applicator, the applicator comprises a core member 2 having a hole portion 2a, a projection portion 2f and a communication hole 2j, an application member 3 made of an elastic material having a discharge hole 3f, and an inside space 4 between the front end side of the core member 2 and the application member 3, and structured such that the liquid material flows to the discharge hole 3f through a roundabout way via the hole portion 2a, the communication hole 2j and the inside space 4 to cause fluid resistance and that the front face of the projection portion 2f is close to or in contact with the discharge hole 3f to control discharge port of the liquid material.

1 Claim, 13 Drawing Sheets

APPLICATOR

This is a continuation-in-part application of U.S. patent application Ser. No. 10/914,144 filed Aug. 10, 2004, entitled APPLICATOR.

BACKGROUND OF THE INVENTION

1. Field of the Invention

The present invention relates to an applicator for applying a liquid filler.

2. Description of the Conventional Art

Conventionally, the following applicator (for example, referring to Japanese Patent Laid Open No. 2000-262324) is known as a liquid cosmetic extrudable container from which the liquid cosmetic is extruded for use. That is, the applicator comprises a main body cylinder having inside a filling region, in which the liquid cosmetic is filled, and an operating cylinder mounted in the state of being relatively rotatable at a rear end portion of the main body cylinder. In this applicator, the application can be carried out, by a piston arranged in the filling region being advanced when the main body cylinder and the operating cylinder are relatively rotated, the liquid cosmetic being extruded to an front end side by advancing of the piston, and the extruded liquid cosmetic being delivered to an application body mounted on the front end of the main body cylinder, for example a brush or the like, through a pipe being a discharge route connected with the filling region.

SUMMARY OF THE INVENTION

In the liquid cosmetic extrudable container, there is a problem that a hand, clothing or the like may become dirty since the liquid cosmetic may leak from the front end of the container due to an impact, a vibration or the like by falling or the like of the container, or a viscosity change of the liquid cosmetic by a temperature change.

Furthermore, in the liquid cosmetic extrudable container, the liquid cosmetic is often delivered too much when applying the liquid cosmetic, so that it may be difficult to satisfactorily apply the liquid cosmetic.

The present invention was carried out in order to solve the above problems, and has an object to provide an applicator capable of preventing the occurring of dirt due to the leak of the liquid filler, such as the liquid cosmetic, and satisfactorily applying the liquid filler.

An applicator of the present invention comprises a core member installed to a front end portion of a container main body structured such that a liquid material filled in an internal filling region can be extruded toward a front end side, and provided with a hole portion communicating with the filling region and extending to the front end side along an axis, and an application member installed so as to cover the front end side of said core member, wherein an internal space is defined between the front end side of said core member and said application member, wherein said application member is provided with a discharge hole through which a discharge port opened on a front end surface thereof communicates with said internal space, wherein said hole portion of said core member is closed at a front end in an axial direction, wherein an outer periphery in the front end side of said core member is provided with a groove portion extending to a rear side from a front end in a predetermined manner, and the front end side of said core member is provided with a communication hole extending from said hole portion toward an outer side in a radial direction, opening an inner side surface of said groove portion, and communicating with said internal space, and wherein said liquid material in said filling region moves toward an outer side in a radial direction via said hole portion and said communication hole and then turn to move toward said discharge hole.

In such the applicator, a passage of the liquid filler extends toward the discharge hole of the application member through the hole portion, which is provided in the core member, communicates with the filling region, extends to the front end side and is closed at the front end in an axial direction, the communication hole, which communicates with the hole portion, extends toward an outer side in a radial direction and opens an inner side surface of the groove portion, which is provided in an outer periphery in the front end side of the core member and extends to a rear side from a front end side of the core member in a predetermined manner, and the internal space, which is defined between the front end side of the core member and the application member. So, the liquid filler does not flow to the discharge hole straightly at once, but flows to the discharge hole in a roundabout way like that the resistance may be given to the flow. Therefore, even when an impact or a vibration by falling or the like of the container, or a viscosity change or the like of the liquid filler by a temperature change is worked, the leak of the liquid filler can be prevented. Further, excessive discharge of the liquid filler is prevented at a time of application, and thus the discharging amount is made suitable. In this case, it is preferable to structure such that an inner surface of the groove portion and an outer periphery of the hole portion meet together so that the communication hole opens to the groove portion. When such the structure is employed, the communication hole can be easily formed without using an inner mold corresponding to the communication hole, by making an outer mold in such a shape that a part of the groove portion corresponding to the communication hole in the outer mold is in contact with the inner mold, at a time of forming the core member by using the outer mold corresponding to the an outer shape of the core member and the inner mold corresponding to the hole portion of the core member.

In this way, according to the applicator of the present invention, the occurrence of dirt to a hand or clothing or the like by leaking of the liquid filler can be prevented beforehand, and the liquid filler can be satisfactorily applied.

DETAILED DESCRIPTION OF PREFERRED EMBODIMENT

Hereinafter, the suitable preferred embodiment of the applicator of the present invention is explained with referring to FIG. 1 to FIG. 10.

Figure 1:
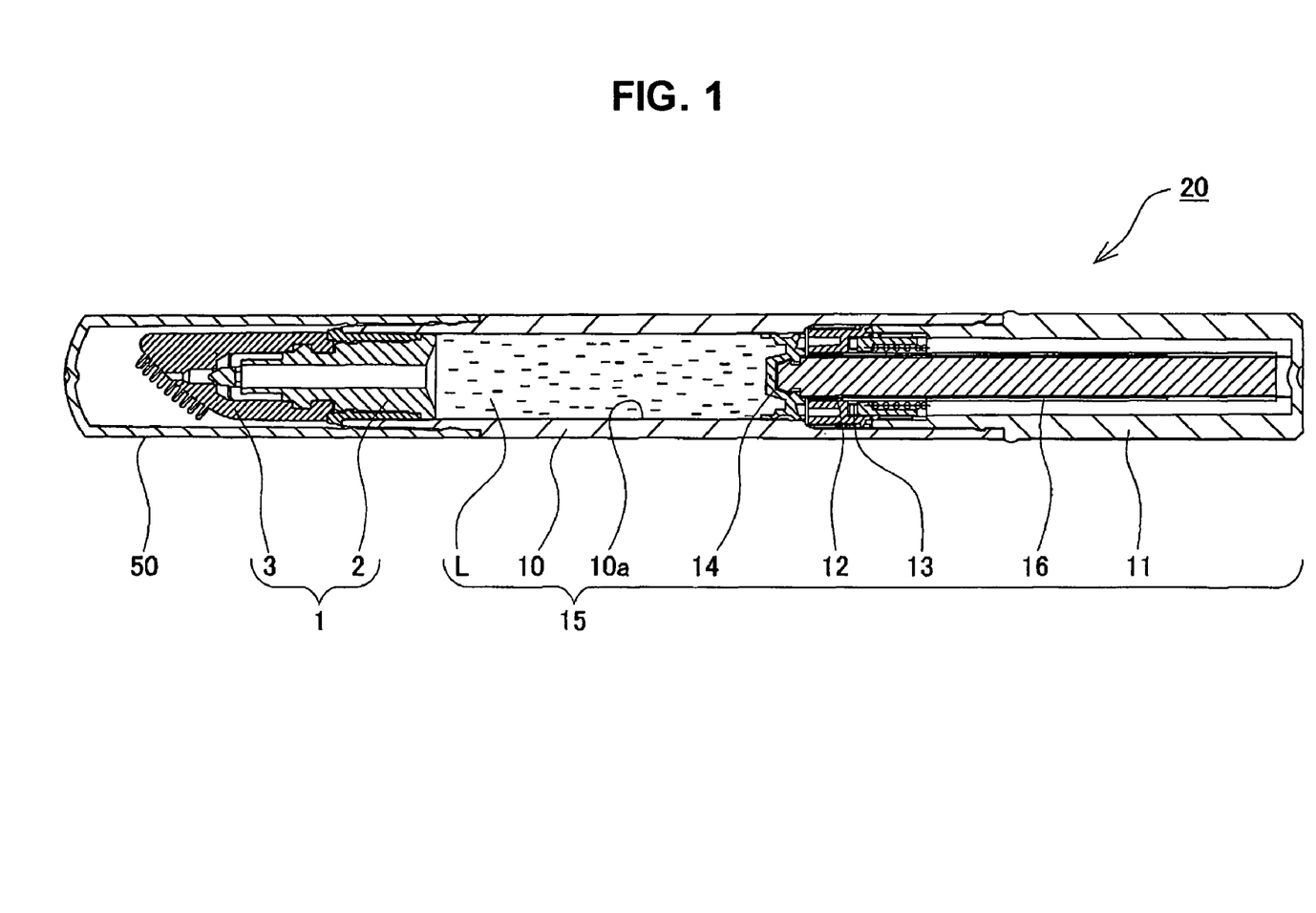
FIG. 1 is a longitudinal sectional view showing a liquid cosmetic extrudable container having an applicator according to an embodiment of the present invention.
Figure 2:
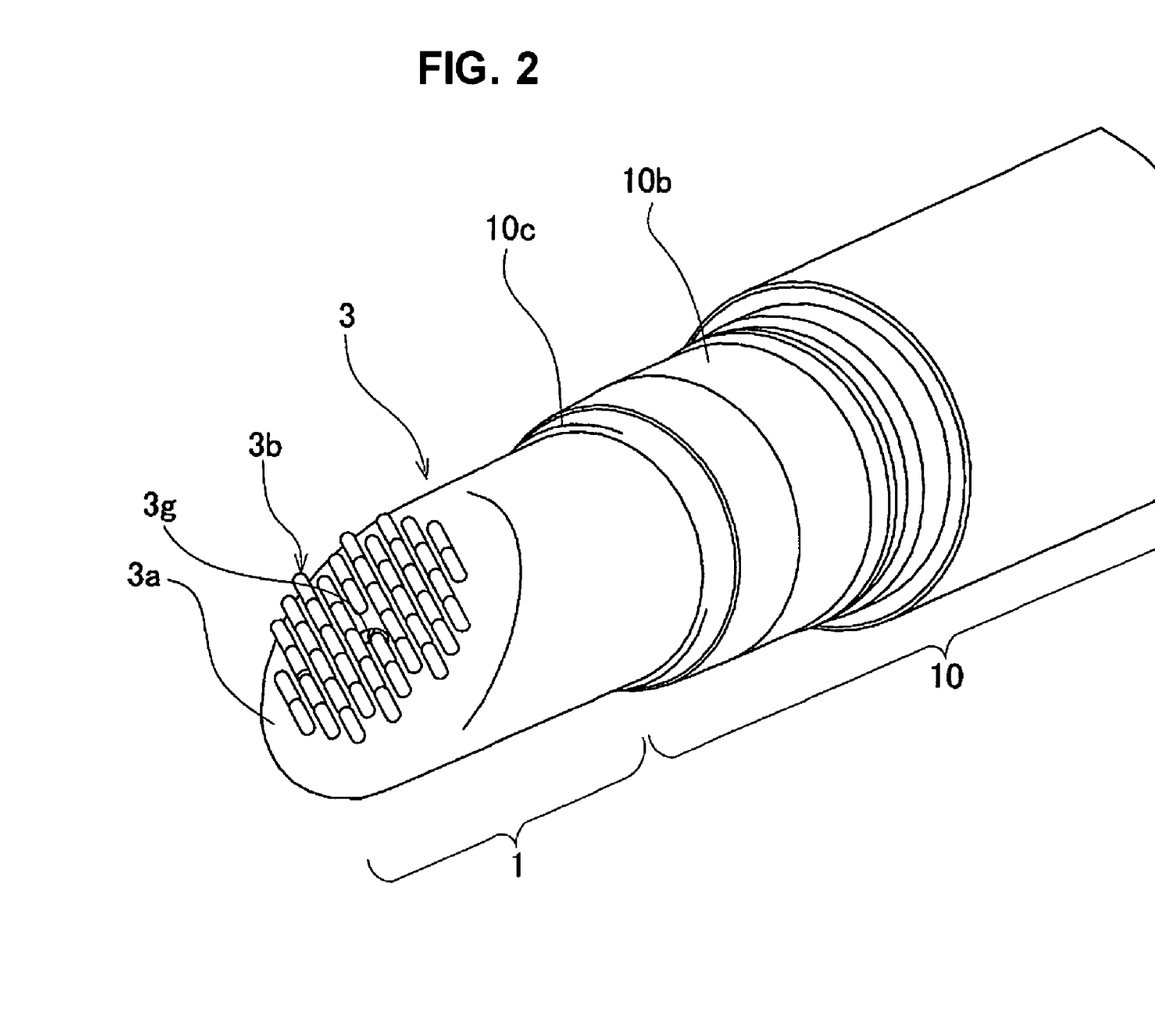
FIG. 2 is a perspective view of an front end portion including an applicator of the liquid cosmetic extrudable container shown in FIG. 1.
Figure 3:
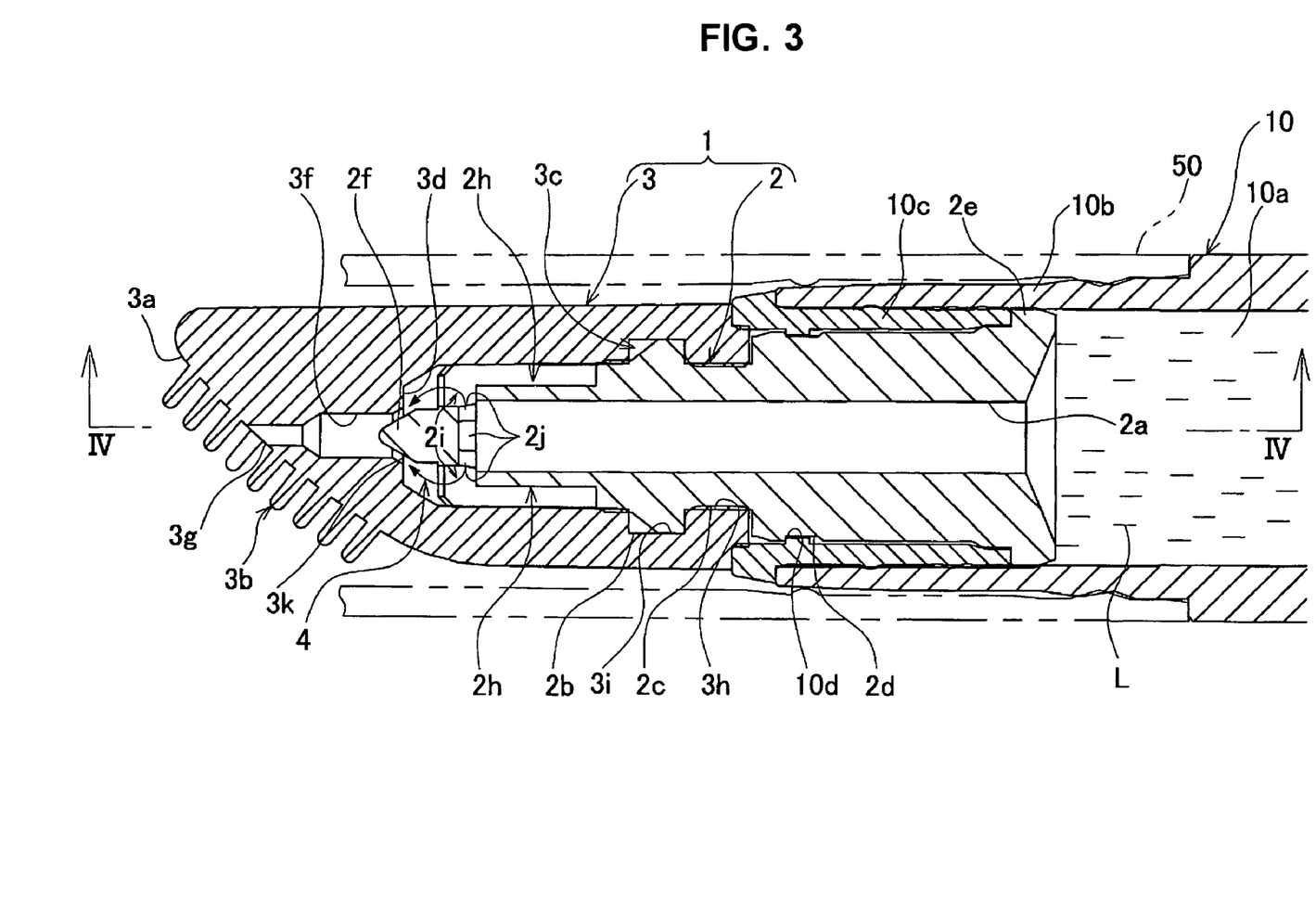
FIG. 3 is a longitudinal sectional view of FIG. 2.
Figure 4:
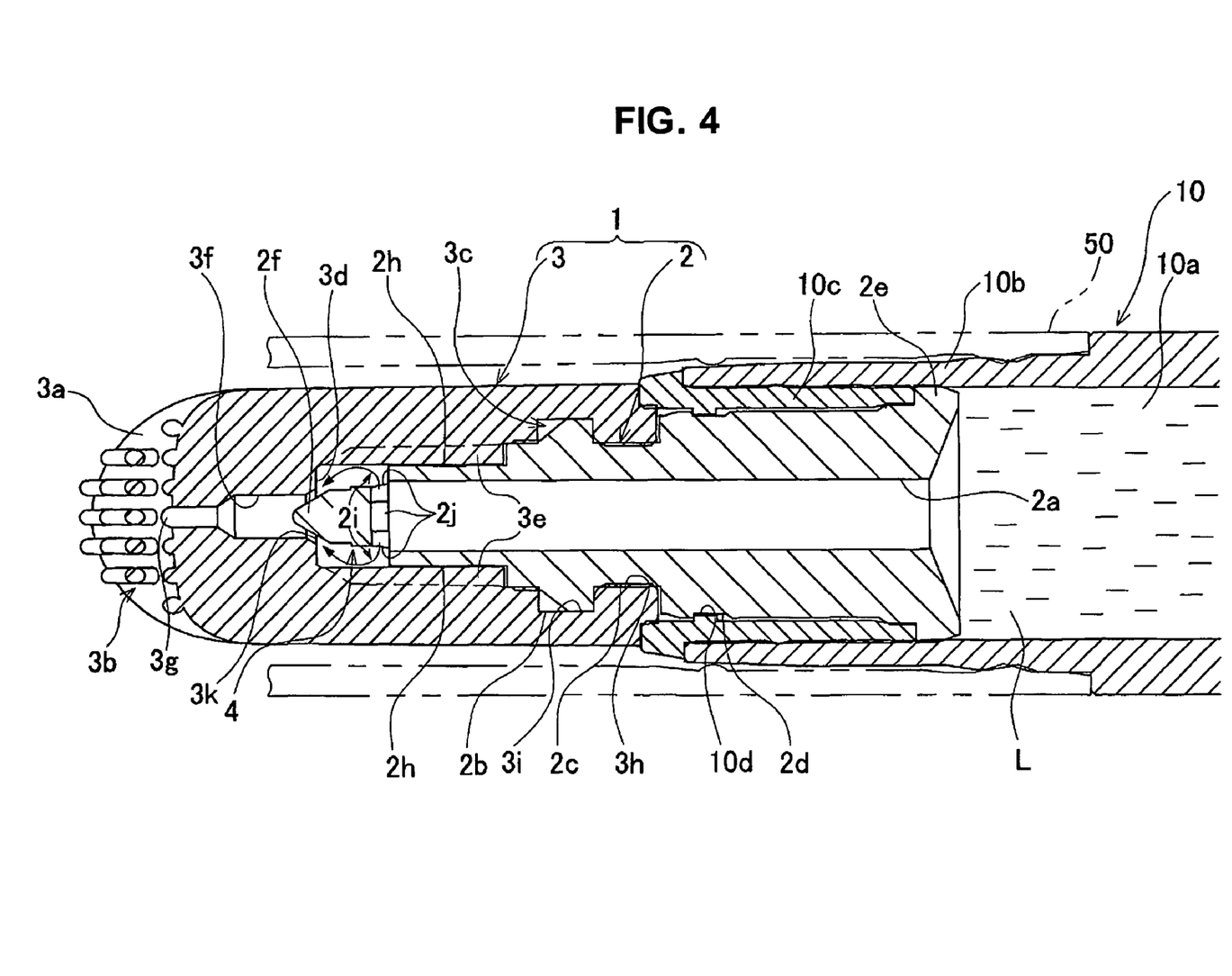
FIG. 4 is a sectional view at an arrow line IV-IV in FIG. 3.
Figure 5:
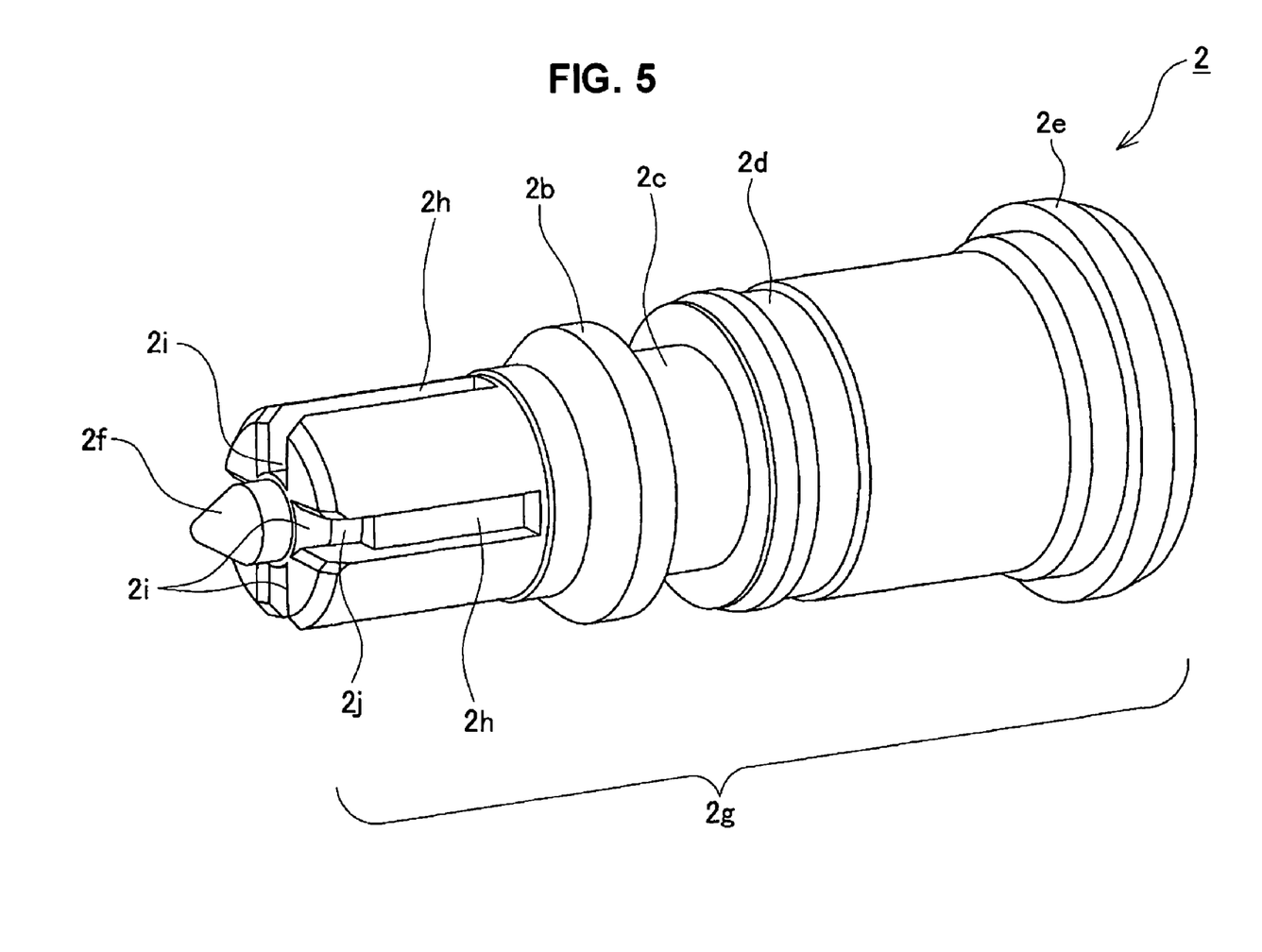
FIG. 5 is a perspective view showing a core member in FIG. 3 and FIG. 4.
Figure 6:
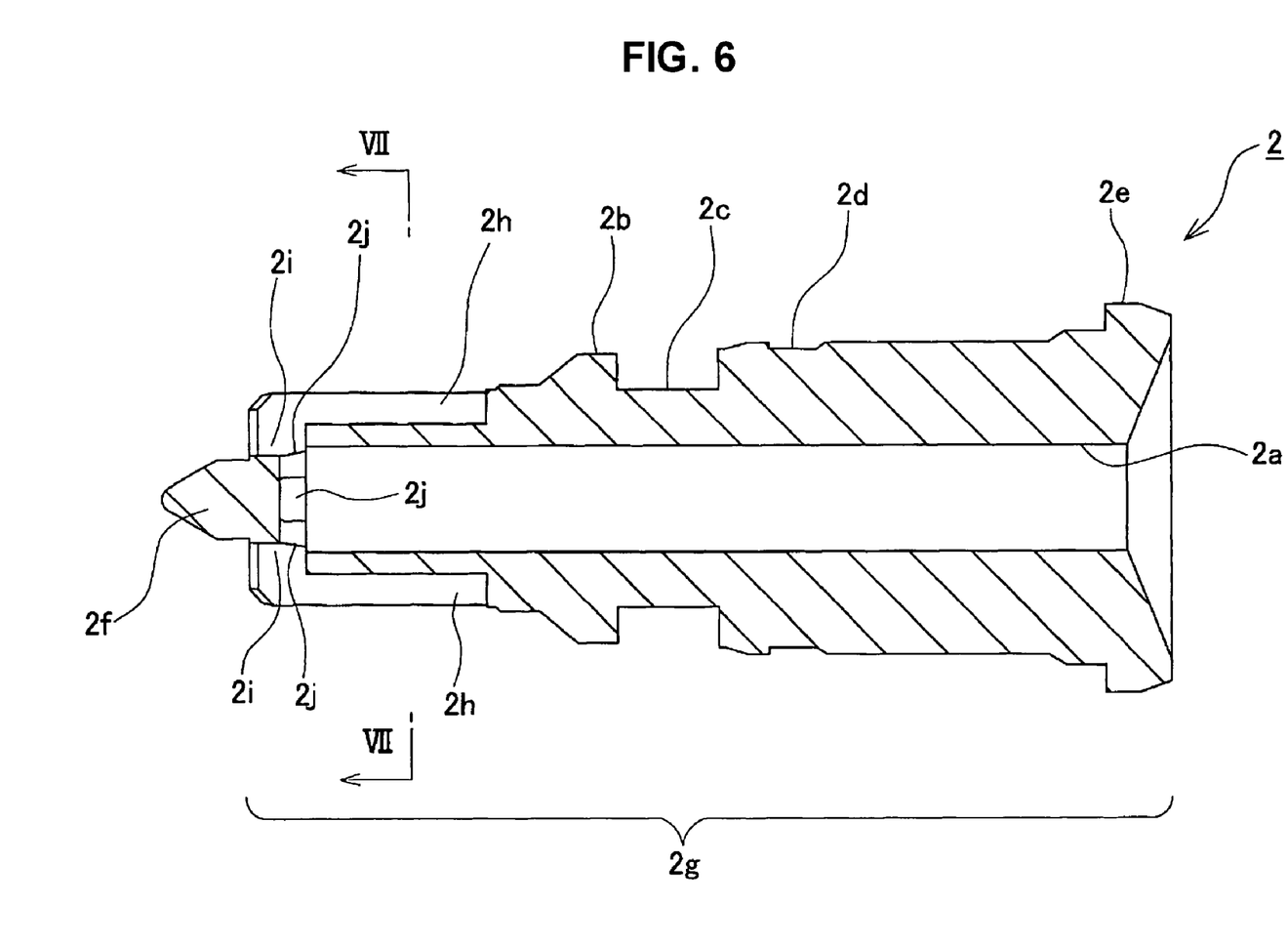
FIG. 6 is a longitudinal sectional view of a core member shown in FIG. 5.
Figure 7:
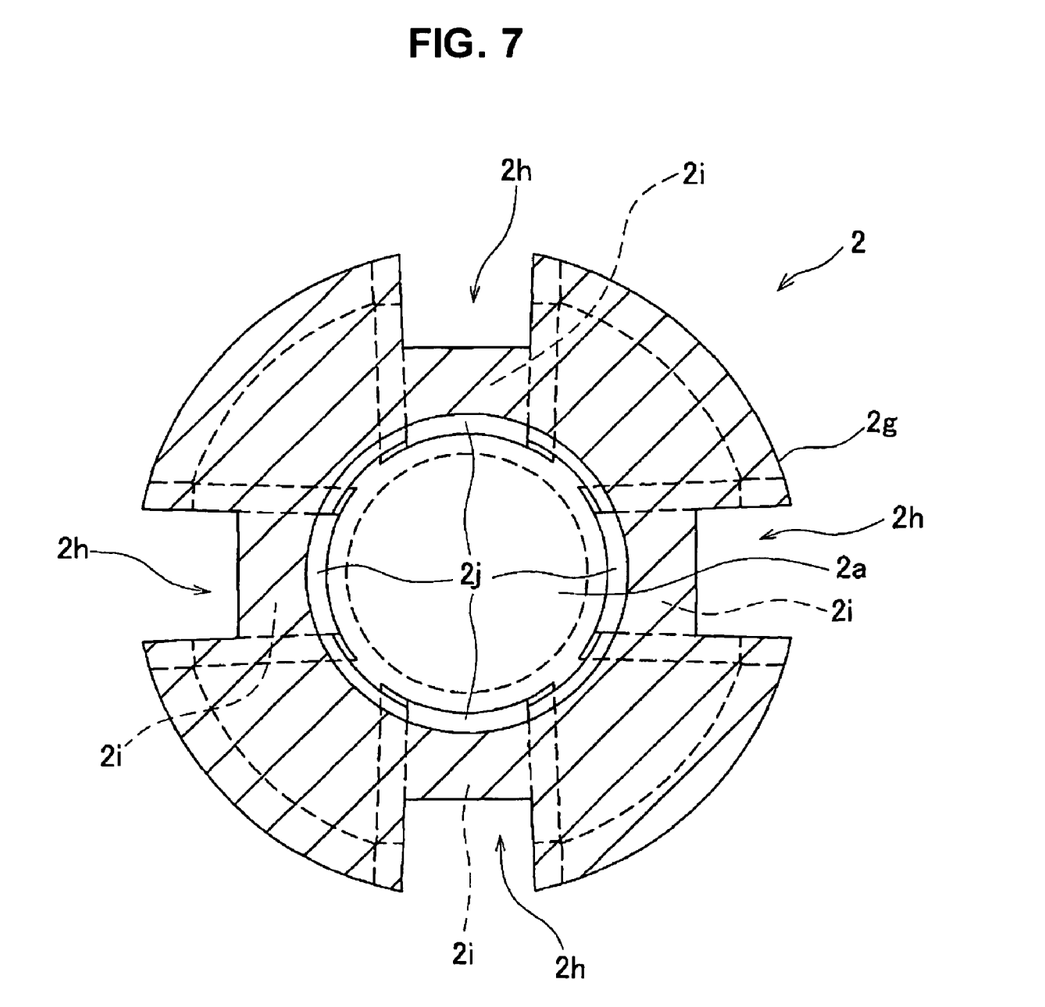
FIG. 7 is a cross sectional view at an arrow line VII-VII in FIG. 6.
Figure 8:
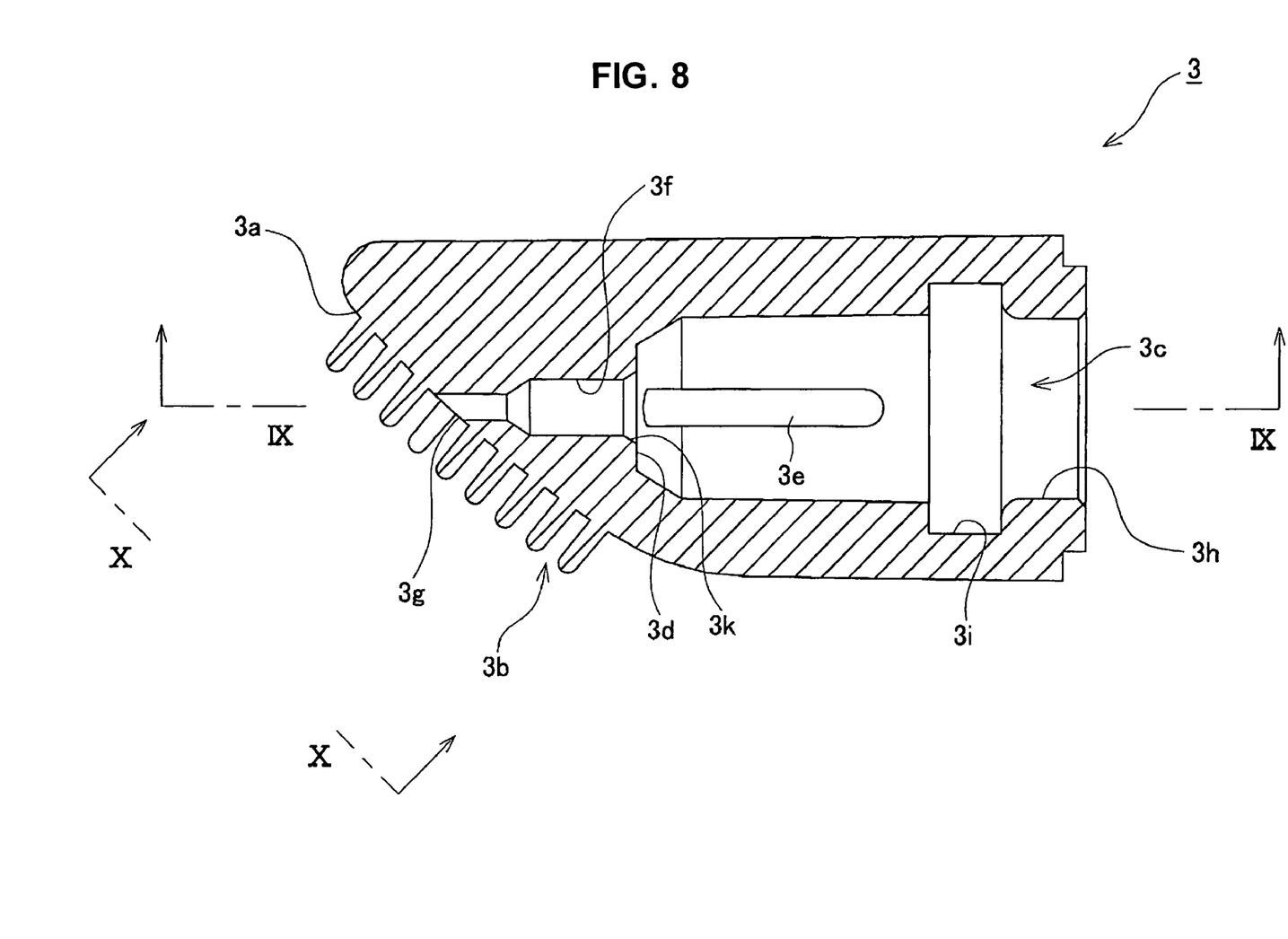
FIG. 8 is a longitudinal sectional view showing an application member in FIG. 3.
Figure 9:
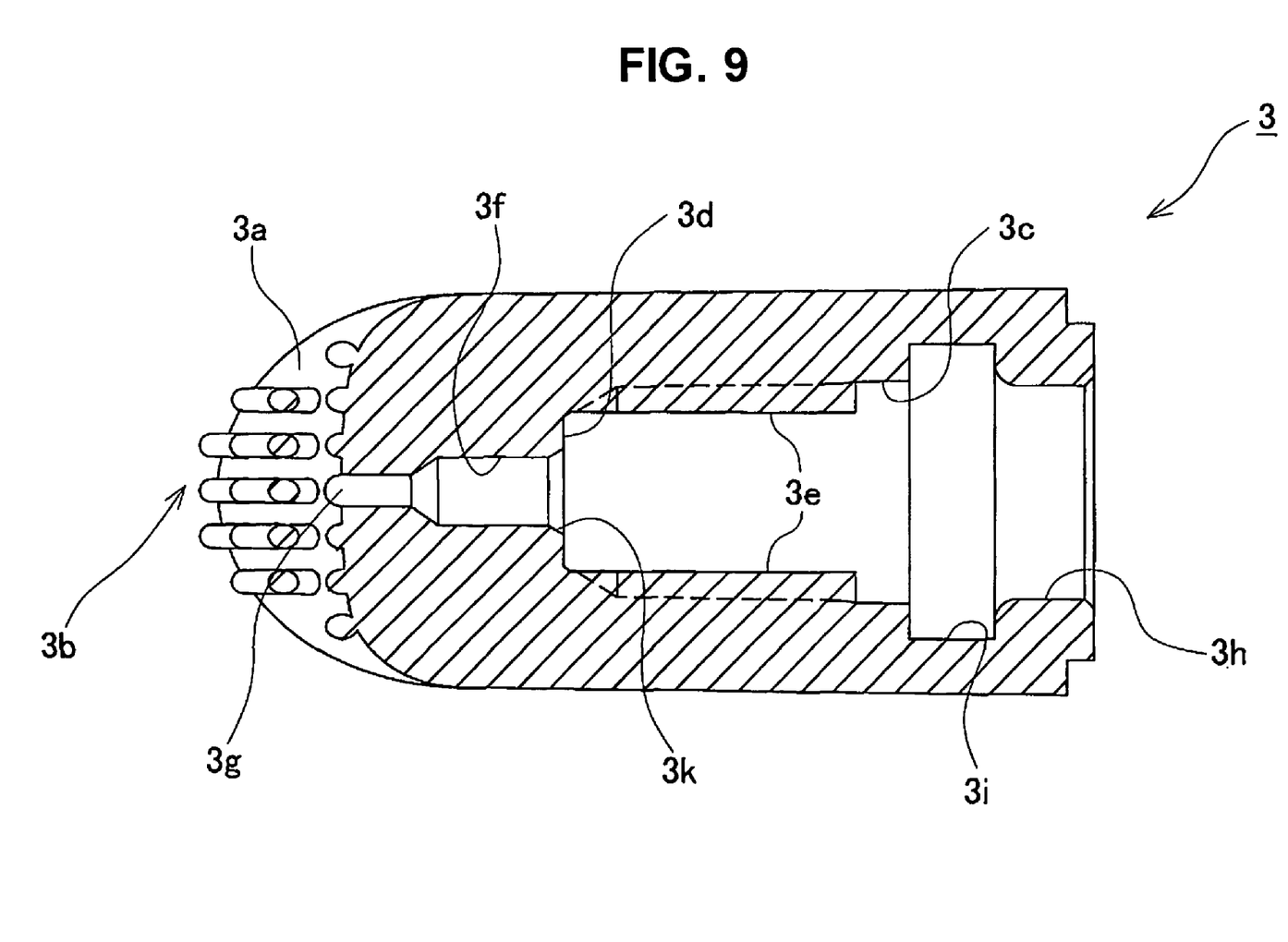
FIG. 9 is a sectional view at an arrow line IX-IX in FIG. 8.
Figure 10:
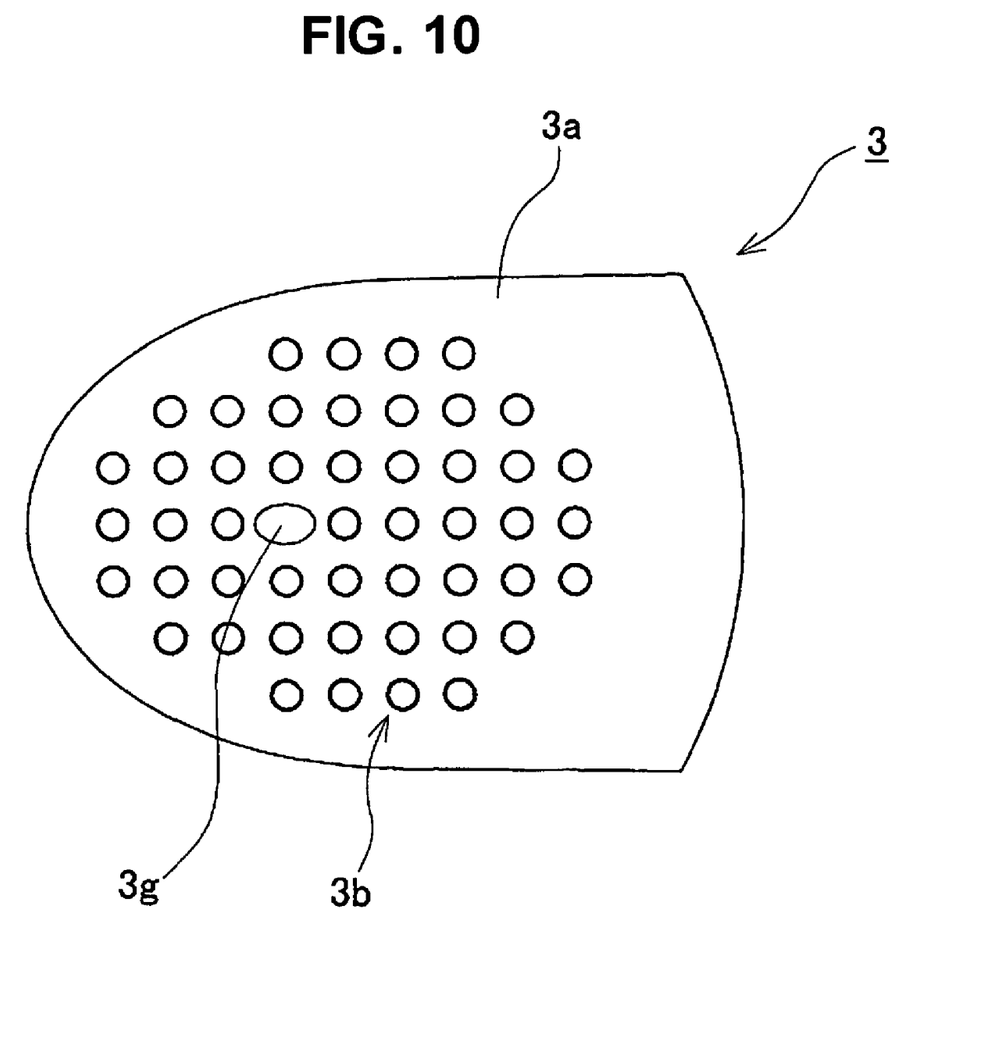
FIG. 10 is a sectional view at an arrow line X-X in FIG. 8.

FIG. 1 to FIG. 10 are each figure showing the applicator according to the embodiment of the present invention. FIG. 1 is a longitudinal cross sectional view showing the liquid cosmetic extrudable container having an applicator according to an embodiment of the present invention. FIG. 2 is a perspective view of the end portion including the applicator of the liquid cosmetic extrudable container. FIG. 3 and FIG. 4 are longitudinal cross sectional views where the cross sectional positions are 90° different respectively from the position of FIG. 2. FIG. 5 to FIG. 7 are each view particularly showing the core member constituting the applicator. FIG. 8 to FIG. 10 are views particularly showing the application member constituting the applicator. The applicator of the embodiment of the present invention is applied to the liquid cosmetic extrudable container.

As shown in FIG. 1, a liquid cosmetic extrudable container 20 has the same constitution as that described in Japanese Patent Laid Open No. 2000-262324, except an applicator 1 constituting a front end portion of the container 20. More particularly, the container 20 has the following constitution as a container body 15. In the container body 15, when a main body cylinder 10 and an operating cylinder 11 are relatively rotated by a user, a piston 14 arranged in a filling region 10a is advanced gradually toward the front end of the main body cylinder 10, and a liquid cosmetic L in the filling region 10a is extruded gradually toward the front end. The main body cylinder 10 has the filling region 10a at the inside, in which the liquid cosmetic L is filled. The operating cylinder 11 is mounted in the state of being relatively rotatable at a rear end portion of the main body cylinder 10. The piston 14 is advanced according to a screw mechanism 12, a rotation stopping mechanism 16, and a ratchet mechanism 13, which are extruding mechanisms constituted in the container 20. The ratchet mechanism allows the piston 14 to rotate only in one direction.

In the embodiment of the present invention, a washing liquid such as a cleansing oil or the like is filled in the filling region 10a of the container body 15. Then, the applicator 1 mounted on the front end portion of the container body 15 is for applying the washing liquid extruded from the filling region 10a by the piston 14 to a skin for effectively removing the dirt or the like of a skin.

The main body cylinder 10 constituting the container body 15 has a cylindrical applicator holding member 10c, which is fitted in a front end cylinder portion 10b and mounted, as shown in FIG. 2 to FIG. 4. In the applicator holding member 10c, an annular projection portion 10d for mounting a core member 2 is formed on an inner peripheral face of a front end side of the applicator holding member 10c, as shown in FIG. 3 and FIG. 4.

The applicator 1 has the core member 2 and an application member 3. The core member 2 is mounted on the main body cylinder 10, for introducing the washing liquid from the filling region 10a to the front end side and controlling the flow of the washing liquid. The application member 3 is mounted so as to cover the end side of the core member 2, for applying the washing liquid from the core member 2.

The core member 2 is made with, for example, polyethylene, polypropylene or other plastic materials. The core member 2 is formed in a stepped approximately cylindrical-shape comprising an annular projection portion and groove portion at its outer periphery, as shown in FIG. 3 to FIG. 7. Further, the core member 2 has a hole portion 2a extending from the rear end face to the front end side along with the axis, as shown in FIGS. 3, 4 and 6.

On the outer peripheral face of the core member 2, as shown in FIG. 3 to FIG. 6, an annular projection portion 2b and an annular groove portion 2c is formed at a position of the middle in an axial direction for mounting an application member 3. Further, an annular groove portion 2d is formed at a position of a rear side of the annular projection portion 2b and the annular groove portion 2c. An annular projection portion 10d of the applicator holding body 10c is fitted in the annular groove portion 2d. Furthermore, an annular collar portion 2e is formed at a rear end position. The annular collar portion 2e outwardly projects and contacted with a rear end face of the applicator holding body 10c.

Furthermore, as shown in FIG. 5 and FIG. 6, the core member 2 has a projection portion 2f projecting frontward at the front end portion thereof, and the rear side from the projection portion 2f is a large diameter portion 2g having the larger diameter than that of the projection portion 2f. The projection portion 2f is for controlling the flow of the washing liquid, and has a tapered conic-shape.

The outer periphery of the large diameter portion 2g of the core member 2 has a groove portion 2h, which extends as much as predetermined length from the front end to the rear side of the large diameter portion 2g and reaches near the annular projection portion 2b. The groove portions 2h, which work as the rotation stopper of the application member 3, are respectively provided at positions separated by 90° in the peripheral direction of the large diameter portion 2g, as shown in FIG. 5 and FIG. 7.

Furthermore, as shown in FIG. 5 and FIG. 6, a second groove portion (a groove portion) 2i is formed at the front end portion of the groove portion 2h of the large diameter portion 2g of the core member 2, and the second groove portion 2i is recessed further inside and reaches the front end face of the large diameter portion 2g. An inside face of the second groove portion 2i is overlapped with the outer peripheral face of the hole portion 2a, as shown in FIG. 6, and a communication hole 2j is opened at the overlapping position, as shown in FIG. 5 to FIG. 7. The communication hole 2j communicates with the hole portion 2a and the outside of the core member 2 (in other words, extends from the front end of the hole portion 2a to the outside in a radius direction to communicate with the outside of the core member 2).

The core member 2 having such the constitution can be manufactured by the following manufacturing method. That is, the method comprises, using the outer mold corresponding to the external shape of the core member 2 and the inner mold corresponding to the hole portion 2a of the core member 2, making the portion corresponding to the communication hole 2j of the second groove portion 2i of the outer mold to be in the outer mold-shape contacting with the inner mold, pouring a predetermined resin into the outer mold, and solidifying and demolding it. Therefore, the communication hole 2j can be easily formed without the inner mold corresponding to the communication hole 2j, and thus the manufacturing cost can be reduced.

The application member 3 is molded with the soft elastic material, such as a silicone rubber or the like. The application member 3 is constituted to have an approximately cylindrical-shape, and a front end face 3a of the application member 3 has an inclined face being suitable for application, as shown in FIG. 2 to FIG. 4, FIG. 8 and FIG. 9. On the inclined front end face 3a, a group of many projections having a brushing function is provided by integral molding.

The application member 3 has a recessed portion 3c recessed from the rear end face, as shown in FIGS. 3, 4, 8 and 9. The recessed portion 3c has the shape corresponding to a round external shape of the portion from the front end of the large diameter portion 2g to the annular groove portion 2c, as shown in FIG. 4. Thereby, the portion from the front end of the large diameter portion 2g to the annular groove portion 2c can be fitted in this recessed portion 3c (refer to FIG. 5 and FIG. 6). The recessed portion 3c also has an annular projection portion 3h at the position of the rear end portion, and an annular groove portion 3i at the position adjacent to the front side of the annular projection portion 3h. The annular projection portion 3h is fitted in the annular groove portion 2c of the core member 2, and the annular groove portion 3i is fitted in the annular projection portion 2b of the core member 2.

Furthermore, the application member 3 has the constitution, in which the portion corresponding to the external shape of the front end of the large diameter portion 2g extends further to the front end side and a bottom face 3d of the recessed portion 3c is formed.

On the peripheral face of the front end side of the recessed portion 3c, a projection line 3e is formed, as shown in FIGS. 4, 8 and 9. The projection line 3e extends as much as predetermined length from the bottom face 3d side to the rear side of the recessed portion 3c, inwardly projects, and enters into and fits in two of four groove portions 2h of the core member 2. The projection line is formed at positions separated by 180° in the peripheral direction of the recessed portion 3c.

Moreover, the application member 3 has a discharge hole 3f. The discharge hole 3f has a smaller diameter than that of the bottom face 3d of the recessed portion 3c and communicates with the bottom face 3d and the front end face 3a. The discharge hole 3f is constituted to have a circular cross section. An opening on the front end face 3a of the discharge hole 3f is a discharge port 3g, and a group of many projections 3b are provided around the discharge port 3g, as shown in FIG. 8 to FIG. 10.

In addition, the application member 3 can be made of one suitably selected from a variety of materials, such as LDPE, thermoplastic elastomer or the like, by the injection molding method, in addition to silicone rubber, ethylenepropylene rubber, isopropylene rubber or the like, by the compression molding method. For example, an application member made by laminating a nylon net and a foamed porous polyurethane sheet and cutting out it can be mounted, and a brush, a hair comb or the like comprising polyester fibers can be also mounted.

Furthermore, the application member 3, the core member 2 and the applicator holding body 10c are assembled as an assembly unit, and are mounted on the main body cylinder 10 after filling the washing liquid in the filling region 10a.

That is, as shown in FIG. 3 and FIG. 4, the core member 2 is mounted on the applicator holding member 10c, by inserting the front end side of the core member 2 from the opening at the rear end of the applicator holding member 10c, butting the annular collar portion 2e against the rear end face of the applicator holding member 10c, and engaging the annular projection portion 10d of the applicator holding member 10c with the annular groove portion 2d. The application member 3 is mounted on the core member 2, by externally putting the rear end side of the application member 3 so as to cover the front end side of the core member 2, butting the rear end face of the application member 3 against the front end face of the applicator holding body 10c, respectively engaging the annular projection portion 3h with the annular groove portion 2c of the core member 2, the annular groove portion 3i with the annular projection portion 2b of the core member 2, and the two projection lines 3e with the groove portions 2h of the core member 2 so as to constitute the rotation stopper. Thereby, the assembly unit having the application member 3, the core member 2 and the applicator holding member 10c is constituted, and the applicator holding body member 10c constituting the assembly unit is fitted in the front end cylindrical portion 10b of the main body cylinder 10. Then, the assembly unit is mounted on the main body cylinder 10 where the annular collar portion 2e of the core member 2 is airtightly bonded to the inner peripheral face of the main body cylinder 10.

In this state, the hole portion 2a of the core member 2 communicates with the filling region 10a.

Moreover, in this state, a predetermined inside space 4 is formed between the bottom face 3d side of the recessed portion 3c of the application member 3 and the front end portion of the core member 2, more particularly, between the bottom face 3d side of the recessed portion 3c of the application member 3, and the projection portion 2f and the second groove portion 2i of the core member 2. With this inside space 4, the communication hole 2j opening at the second groove portion 2i of the core member 2 communicates, and an opening 3k at the recessed portion 3c side (the inside space 4 side) of the discharge hole 3f of the application member 3 communicates.

Furthermore, in this state, the projection portion 2f of the core member 2 projects toward the discharge hole 3f of the application 3, the front end portion of the projection portion 2f enters into the discharge hole 3f, and the outer face of the front end portion is positioned close to the discharge hole 3f with keeping a predetermined space.

Moreover, the applicator 1 having the core member 2 and the application member 3 is covered and protected by a cap 50 which is detachably mounted on the front end cylindrical portion 10b of the main body cylinder 10, as shown in FIG. 1.

Next, the case when the washing liquid is applied using a liquid cosmetic extrudable container 20 having such the applicator 1 is explained with reference to FIG. 3 and FIG. 4. When the washing liquid is extruded from the filling region 10a by an operation of a user, a passage of the washing liquid extends toward the discharge hole 3f of the application member 3 through the hole portion 2a and the communication hole 2j of the core member 2 and the inside space 4. So, the washing liquid does not flow toward the discharge hole 3f straightly at once, but flows in a roundabout way so that the resistance may be given to the flow, as shown with an arrow in the figure. In addition, the outer face of the projection portion 2f of the core member 2 has a constitution being close to the discharge hole 3f, so that the discharge hole 3f is narrowed or closed.

Therefore, it can be prevented to deliver too much the washing liquid in application so that the delivering amount becomes suitable, and thus the washing liquid is satisfactory applied.

At this time, since a group of many projections 3b having a brushing function is arranged around the discharge port 3g of the application member 3, the dirt of skin, especially, the dirt of pores can be effectively removed by a group of these projections 3b and the washing liquid. Furthermore, since a group of the projections 3b projects in the direction inclined with respect to the axial direction of the application member 3 (a group of the projections 3b are vertically provided with respect to the inclined end face 3a), the dirt can be removed much more effectively.

Furthermore, at this time, since the rotation stopper of the application member 3 is constituted by the projection line 3e of the application member 3 and the groove portion 2h of the core member 2, the application member 3 is not rotated at the time of applying, so that the washing liquid can be applied much more satisfactory.

Furthermore, even when an impact or a vibration by falling or the like, or a viscosity change or the like of the washing liquid by a temperature change is worked to the liquid cosmetic extrudable container 20 having such the applicator 1, the leak of the washing liquid can be prevented since the discharge hole 3f is narrowed and the passage of the washing liquid is made roundabout. Therefore, it can be prevented beforehand that a hand, clothing or the like becomes dirty.

In addition, the space between the outer face of the projection portion 2f of the core member 2 and the discharge hole 3f can be controlled depending on, for example, viscosity of the washing liquid or the like.

In this case, in each of the above embodiments, the projection portion 2f (22f) of the core member 2 (22) is entered into the discharge hole 3f (23f) of the application member 3 (23), since it is especially effective to prevent the leak of the washing liquid. However, the projection portion 2f (22f) may not be entered into the discharge hole 3f (23f).

Furthermore, in each of the above embodiments, the projection hole 3f (23f) of the application member 3 (23) has a circular shape (the discharge port 3g has an oval shape at this time), and the projection portion 2f (22f) of the core member 2 (22) has the conic shape, because it is easy to manufacture and control the flow of the washing liquid. However, the discharge hole 3f (23f) may have an oval shape (the discharge port 3g has the circular shape at this time), or a rectangular shape, or the like, and the projection portion 2f (22f) may have a pyramidal shape or the like, for example.

Furthermore, in each of the above embodiments, although the application member 3 (23) is mounted on the core member 2 (22), the application member 3 (23) can be directly mounted on the main body 10 (60) or the like, for example.

By the way, in each of the above embodiments, the washing liquid is used as an example of the liquid filler, since it is especially suitable. However, it is not limited to the washing liquid, but the liquid filler may also be a cosmetic solution, a nail care solution, a nail remover, a mascara, an anti ageing solution, a hair color, a cosmetic for hair, an oral care solution, a massage oil, a keratotic plug softening liquid, an ink of a writing tool such as a marking pen or the like, a liquefied medicine, a muddy material, a shoe polish, or the like.

Figure 11:
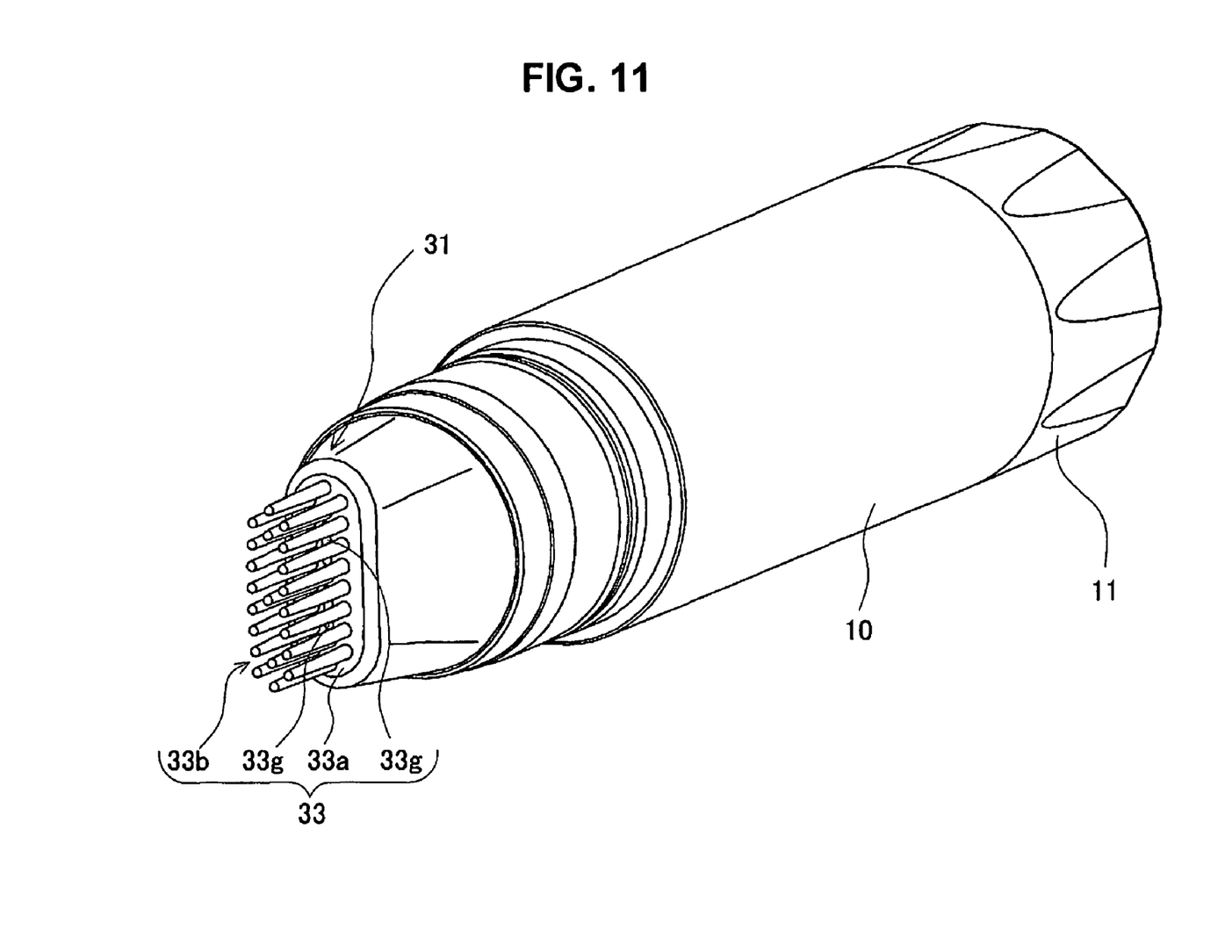
FIG. 11 is a perspective view showing another applicator applied to the liquid cosmetic extrudable containers in FIG. 1.
Figure 12:
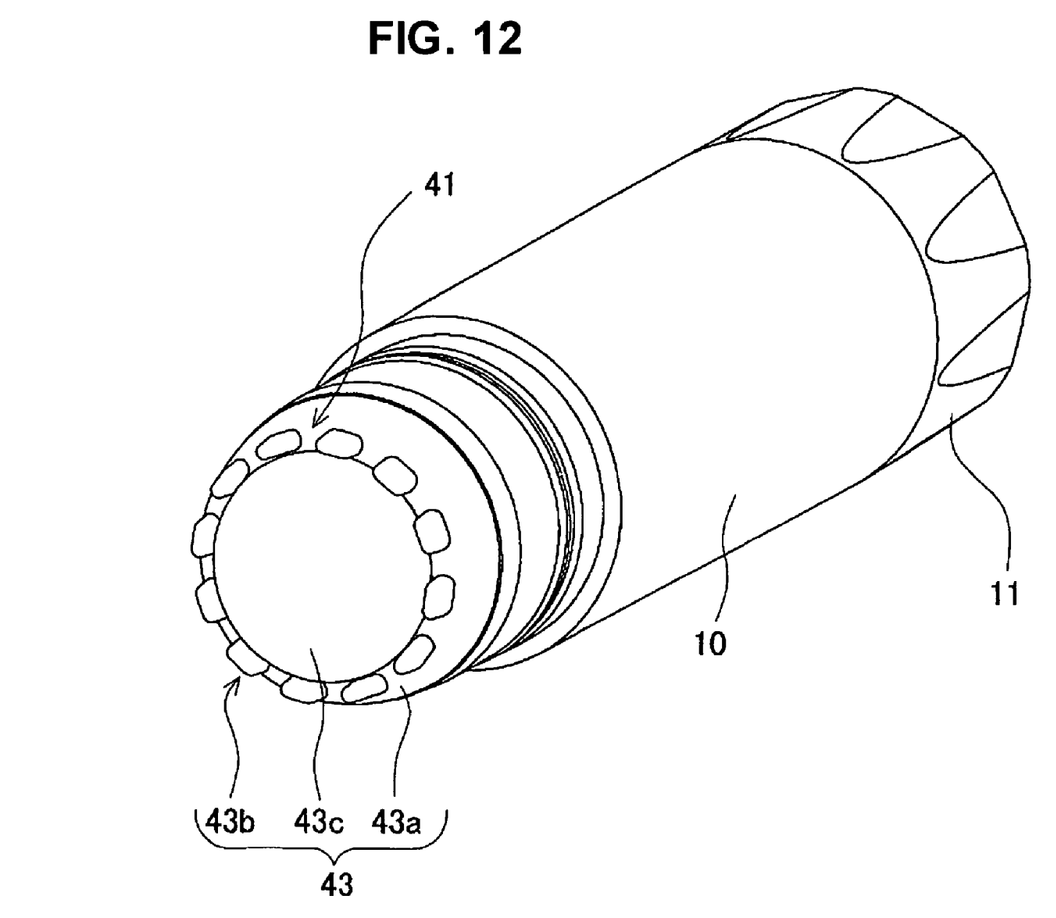
FIG. 12 is a perspective view showing another applicator applied to the liquid cosmetic extrudable containers in FIG. 1.
Figure 13:
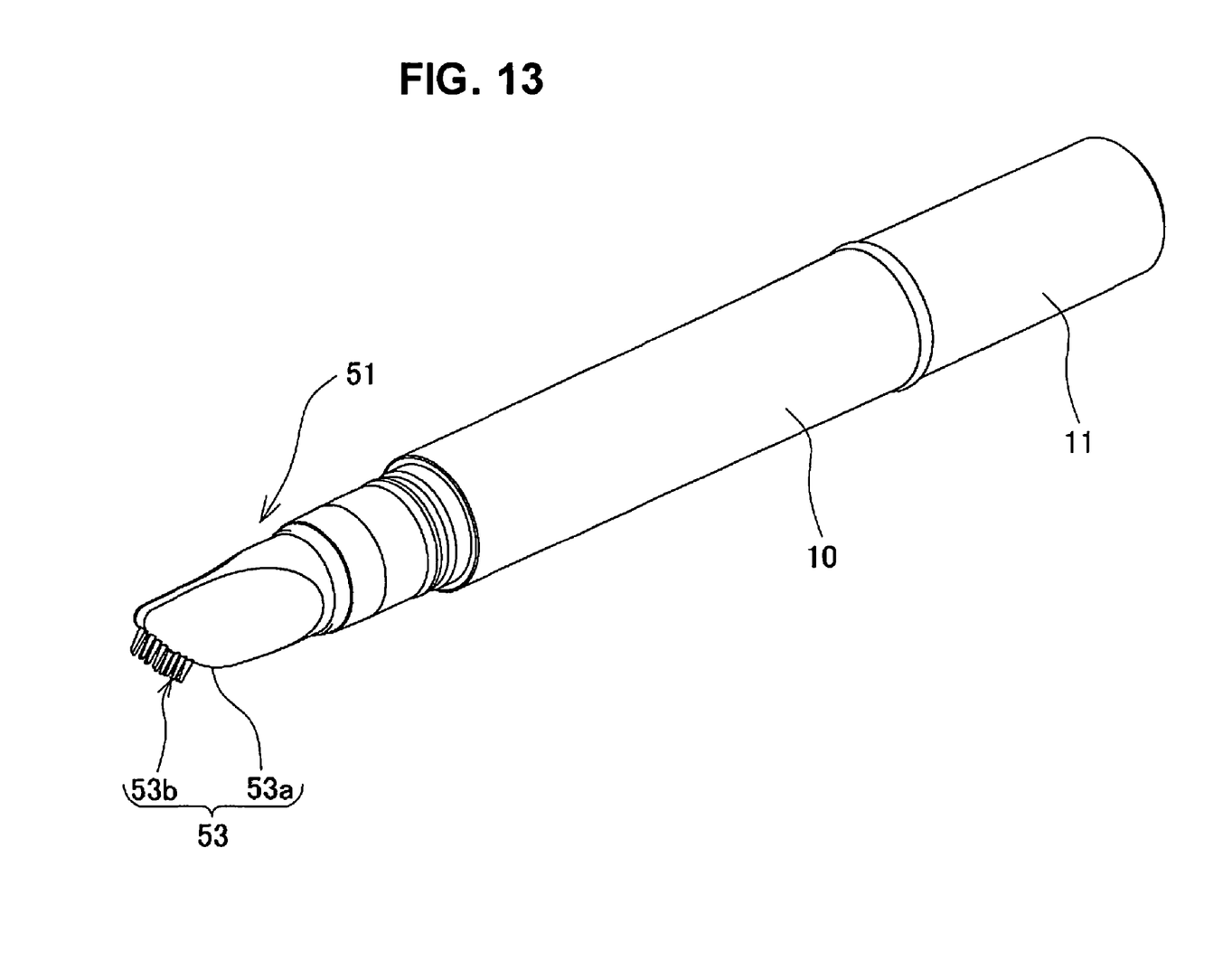
FIG. 13 is a perspective view showing another applicator applied to the liquid cosmetic extrudable containers in FIG. 1.

FIG. 11 to FIG. 13 are perspective views showing other applicators 31, 41, 51, which are applied to the liquid cosmetic extrudable containers of FIG. 1 and FIG. 12. The core members constituting these applicators 31, 41, 51 are the same as those of FIG. 1 and FIG. 12.

In the applicator 31 shown in FIG. 11, a front end face 33a of an application member 33 is constituted to have a vertical face with respect to the axis of the application member 33, and have a long ellipse shape as shown in the figure. Further, a discharge port 33g of the front end face 33a has an ellipse shape being similar to the shape of the front end face 33a and having the small diameter, and plural discharge ports 33g (two in the figure) are opened on the front end face 33a. Further, a group of projections 33b around these discharge ports 33g has a long pectinate shape.

Furthermore, in the applicator 41 shown in FIG. 12, a sponge-like application body 43c with a large diameter covering the discharge port is mounted on a front end face 43a of an application member 43, and a group of warty projections 43b are annularly arranged around the application body 43c.

Furthermore, in the applicator 51 shown in FIG. 13, an application member 53 is tapered toward a front end side so that a front end face 53a of the application member 53 has a narrow width. A group of projections 53b in a long pectinate shape is arranged in parallel to the longitudinal direction of the front end face 53a having a narrow width, and a group of the projections 53b are provided so as to position around a discharge port. A group of the projections 53b is provided so as to project in the direction inclined with respect to the axial direction of the application member 53.

Then, when such the applicators 31, 41, 51 having constitutions shown in FIG. 11 to FIG. 13 are suitably selected according to the above various liquid materials filled therein, the applicator can be used most suitably. By the way, when a group of the projections projects in the direction inclined with respect to the axial direction of the application member, as shown in FIG. 13, there is an advantage that functions of a group of the projections can be diversified.

Although the present invention is explained in the above based on the embodiments, the present invention is not limited to the above embodiments. For example, as for the extruding mechanism of the liquid material extrudable container used for extruding the above various liquid materials, it is not limited to the rotational type extruding mechanism mentioned above, but for example, a knock type extruding mechanism or the like may be used. Furthermore, the above various applicators 1, 21, 31, 41, 51 can be applied to a liquid material extrudable container of a simple squeeze type, such as a tube, a soft bottle or the like. When these applicators 1, 21, 31, 41, 51 are suitably selected according to various container types (an extruding type) and various liquid materials filled therein, the applicators can be used most suitably.

What is claimed is:

1. An applicator comprising:
   a container main body structured such that a liquid filler in an internal filling region can be extruded toward a front end side of a core member;
   the core member installed to a front end portion of said container main body, and provided with a hole portion communicating with said filling region and extending to the front end side along an axis; and
   an application member secured to said core member so as to cover the front end side of said core member,
   wherein an internal space is defined between the front end side of said core member and an interior of said application member,
   wherein said application member is provided with a discharge hole having a discharge port that is open on an inclined end surface of said application member and an opening that communicates with said internal space,
   wherein said hole portion of said core member is closed at a front end in an axial direction by a tapered, conical-shaped projection portion,
   wherein said core member is provided in an outer periphery of the front end side with groove portions extending axially from the front end side to a rear side by a given length and communicating with said internal space, and is provided between a front end of said hole portion and a rear end of said projection portion with communication holes extending outward in a radial direction and communicating said groove portions to said hole portion, wherein said groove portions further are recessed from the outer periphery of the front end side and extend radially to the communication holes,
   a front end of said projection portion is inserted into said opening in said application member with a given fixed clearance, and
   wherein said liquid filler in said filling region flows through said hole portion, said communication holes, said groove portions, said internal space, said opening, and said discharge hole to said discharge port.

* * * * *